US008885898B2

(12) United States Patent
Liu et al.

(10) Patent No.: US 8,885,898 B2
(45) Date of Patent: Nov. 11, 2014

(54) MATCHING OF REGIONS OF INTEREST ACROSS MULTIPLE VIEWS

(75) Inventors: Meizhu Liu, Gainesville, FL (US); Le Lu, Chalfont, PA (US); Vikas C. Raykar, Conshohocken, PA (US); Marcos Salganicoff, Bala Cynwyd, PA (US); Matthias Wolf, Coatesville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 524 days.

(21) Appl. No.: 13/267,095

(22) Filed: Oct. 6, 2011

(65) Prior Publication Data

US 2012/0088981 A1    Apr. 12, 2012

Related U.S. Application Data

(60) Provisional application No. 61/390,646, filed on Oct. 7, 2010.

(51) Int. Cl.
| | |
|---|---|
| G06K 9/00 | (2006.01) |
| G06T 7/00 | (2006.01) |
| G06K 9/62 | (2006.01) |
| A61B 6/03 | (2006.01) |
| A61B 8/13 | (2006.01) |

(52) U.S. Cl.
CPC ............ *G06K 9/6215* (2013.01); *G06T 7/0014* (2013.01); *A61B 6/032* (2013.01); *G06T 7/0024* (2013.01); *A61B 6/037* (2013.01); *G06T 2207/30032* (2013.01); *A61B 8/13* (2013.01); *G06T 2207/20081* (2013.01); *G06T 2207/10072* (2013.01)
USPC ........................................................ 382/128

(58) Field of Classification Search
CPC .......... A61B 6/032; A61B 6/037; A61B 8/13; G06K 9/6215; G06T 2207/10072; G06T 2207/20081; G06T 2207/30032; G06T 7/0014; G06T 7/0024
USPC ........................................................ 382/128
See application file for complete search history.

(56) References Cited

U.S. PATENT DOCUMENTS 7,333,645 B1 *    2/2008    Mitchell et al. ............... 382/128

OTHER PUBLICATIONS

Jinbo Bi; Dijia Wu; Le Lu; Meizhu Liu; Yimo Tao; Wolf, M.; , "AdaBoost on low-rank PSD matrices for metric learning," Computer Vision and Pattern Recognition (CVPR), 2011 IEEE Conference on , vol., No., pp. 2617-2624, Jun. 20-25, 2011.

(Continued)

*Primary Examiner* — Tom Y Lu
(74) *Attorney, Agent, or Firm* — Peter R. Withstandley

(57) ABSTRACT

Described herein is a framework for multi-view matching of regions of interest in images. According to one aspect, a processor receives first and second digitized images, as well as at least one CAD finding corresponding to a detected region of interest in the first image. The processor determines at least one candidate location in the second image that matches the CAD finding in the first image. The matching is performed based on local appearance features extracted for the CAD finding and the candidate location. In accordance with another aspect, the processor receives digitized training images representative of at least first and second views of one or more regions of interest. Feature selection is performed based on the training images to select a subset of relevant local appearance features to represent instances in the first and second views. A distance metric is then learned based on the subset of local appearance features. The distance metric may be used to perform matching of the regions of interest.

29 Claims, 11 Drawing Sheets

(56) References Cited

OTHER PUBLICATIONS

A. Bar-Hille, T. Hertz, N. Shental and D. Weinshall, "Learning a Mahalanobis metric from equivalence constraints", Journal of Machine Learning Research, 6 (2005) 937-965. 2617, 2623.

A. Bar-Hillel and D. Weinshall, "Learning Distance Function by Coding Similarity", ICML, 2007.

J. David, B. Kulis, P. Jain, S. Sra and I.S. Dhillon, "Information-Theoretic Metric Learning", ICML, pp. 209-216, 2007.

Eric P. Xing, Andrew Y. Ng, Michael I. Jordan and Stuart Russell, "Distance Metric Learning, with Application to Clustering with Side-Information", NIPS, vol. 15, pp. 505-512, 2003.

Y. Freund, R. Iyer, R. Schapire, and Y. Singer, "An Efficient Boosting Algorithm for Combining Preferences", Journal of Machine Learning Research 4 (2003) 933-969.

Yoav Freund, Robert E. Schapire, "A decision-theoretic generalization of on-line learning and an applicatoin to boosting", Journal of Computer and System Sciences, 55(1): 119-139, 1997.

Glenn Fung, Murat Dundar, Balaji Krishnapuram, R. Bharat Rao, "Multiple Instance Learning for Computer Aided Diagnosis", NIPS, pp. 425-432, 2006.

Hastie, T.; Tibshirani, R.; , "Discriminant adaptive nearest neighbor classification," Pattern Analysis and Machine Intelligence, IEEE Transactions on , vol. 18, No. 6, pp. 607-616, Jun. 1996.

Xiaofei He; King, O.; Wei-Ying Ma; Mingjing Li; Hong-Jiang Zhang; , "Learning a semantic space from user's relevance feedback for image retrieval," Circuits and Systems for Video Technology, IEEE Transactions on , vol. 13, No. 1, pp. 39-48, Jan. 2003.

Zhaoqiang Lai, Jiaxi Hu, Chang Liu, Vahid Taimouri, Darshan Pai, Jiong Zhu, Jianrong Xu, and Jing Hua, "Intra-Patient Supine-Prone Colon Registration in CT Colonography Using Shape Spectrum", MICCAI, pp. 332-339, 2010.

H. Muller, T. Pun, and D. Squire, "Learning from user behavior in image retrieval: application of market basket analysis", International Journal of Computer Vision, 56(1-2):65-77, 2004.

H. Peng, F. Long and C. Ding, "Feature selection based on mutual information; Criteria of max-dependency, max-relevance, and min-redundancy", IEEE Trans. Pattern Anal. Mach. Intell., 27(8):1226-1238, 2005.

Romer Rosales and Glenn Fung, "Learning Sparse Metrics via Linear Programming", Proceedings of ACM International Conference on Knowledge Discovery and Data Mining, 2006.

Holger Roth, Jamie McClelland, Marc Modat, Darren Boone, Mingxing Hu, Sebastien Ourselin, Greg Slabaugh, Steve Halligan, and David Hawkes, "Establishing Spatial Correspondence between the Inner Colon Surfaces from Prone and Supine CT Colonography", MICCAI, pp. 497-504, 2010.

Robert E. Schapire, Yoram Singer, "Improved Boosting Algorithms Using Confidence-rated Predictions", Machine Learning, 37(3): 297-336, 1999.

Chunhua Shen, Junae Kim, Lei Wan, Anton van den Hengel, "Positive Semidefinite Metric Learning with Boosting", Advances in Neural Information Processing Systems, 22, 2009.

C. Shen, A Welsh and L. Wang, "PSDBoost: matrix generation linear programming for positive semidefinite matrices learning", Advances in Neural Information Processing Systems, 21, 2008.

Shiming Xiang, Feiping Nie, Changshui Zhang, "Learning a Mahalanobis Distance Metric for Data Clustering and Classification", Pattern Recognition, 41(12):3600-3612, 2008.

Jie Yu; Amores, J.; Sebe, N.; Radeva, P.; Qi Tian; , "Distance Learning for Similarity Estimation," Pattern Analysis and Machine Intelligence, IEEE Transactions on , vol. 30, No. 3, pp. 451-462, Mar. 2008.

Zhou, S.K.; Georgescu, B.; Comaniciu, D.; Jie Shao; , "BoostMotion: Boosting a Discriminative Similarity Function for Motion Estimation," Computer Vision and Pattern Recognition, 2006 IEEE Computer Society Conference on , vol. 2, No., pp. 1761-1768, 2006.

Hongbin Zhu, Yi Fan, Hongbing Lu, and Zhengrong Liang, "Improving initial polyp candidate extraction for CT colonography", Phys Med Biol. Apr. 7, 2010; 55(7): 2087-2102.

Meizhu Liu, Le Lu, Jinbo Bi, Vikas Raykar, Matthias Wolf, Marcos Salganicoff, "Robust Large Scale Prone-Supine Polyp Matching Using Local Features: A Metric Learning Approach", Medical Image Computing and Computer-Assisted Intervention—MICCAI 2011, Lecture Notes in Computer Science, 2011, vol. 6893/2011, 75-82.

Meizhu Liu, Le Lu, Vikas Raykar, Marcos Salganicoff, "A Robust Feature Integration Approach for Polyp Prone-Supine View Matching and Classification Using Metric Learning", CAD & Knowledge Solutions, Siemens Healthcare, Malvern, PA.

Delphine Nain, Steven Haker, W. Eric L. Grimson, Eric Cosman Jr, William W. Wells, Ron Kikinis, and Carl-Fredrik Westin, "Intra-Patient Prone to Supine Colon Registration for Synchronized Virtual Colonoscopy", MICCAI (2002).

Shijun Wang, et al, "Registration of prone and supoine CT colonography scans using correlation optimized warping and canonical correlation analysis", Medical Physics 36 (2009) 5595-5603.

Ping Li et al., "Registration of central paths and colonic polyps between supine and prone scans in computed tomography colonography: Pilot study", Medical Physics (2004) 31:2912-2923.

Mang, T., Bogoni, L., Salganicoff, M. et al., CT Colonography: Retrospective Evaluation of the Performance of Computer-aided Detection of Colonic Polyps in Tagged and Untagged Preparation. European Congress of Radiology (ECR) (2010).

Greg Slabaugh, Xiaoyun Yang, Xujiong Ye, Richard Boyes and Gareth Beddoe, "A Robust and Fast System for CTC Computer-Aided Detection of Colorectal Lesions", Algorithms 2010, 3, 21-43.

van Ravesteijn, V.F.; van Wijk, C.; Vos, F.M.; Truyen, R.; Peters, J.F.; Stoker, J.; van Vliet, L.J.; , "Computer-Aided Detection of Polyps in CT Colonography Using Logistic Regression," Medical Imaging, IEEE Transactions on , vol. 29, No. 1, pp. 120-131, Jan. 2010.

Le Lu, Matthias Wolf, Jianming Liang, Murat Dundar, Jinbo Bi, and Marcos Salganicoff, "A Two-Level Approach Towards Semantic Colon Segmentation: Removing Extra-Colonic Findings", MICCAI (2009) 1009-1016.

Mark A. Hall, "Correlation-based Feature for Discrete and Numeric Class Machine Learning", ICML (2000) 359-366.

Sun, Yijun, et al, "Local-Learning-Based Feature Selection for High-Dimensional Data Analysis", IEEE TPAMI (2010) 1610-1626.

Eric P. Xing, Andrew Y. Ng, Michael I. Jordan and Stuart Russell, "Distance Metric Learning, with Application to Clustering with Side-Information", NIPS 15 (2002) 505-512.

Freund, Yoav, Schapire, Robert E., "A decision-theoretic generalization of on-line learning and an application to boosting", Comput. Learn. Theory (1995).

Robert E. Schapire, Yoram Singer, "Improved Boosting Algorithms Using Confidence-rated predictions", Machine Learning 37(3) (1999) 297-336.

Vikas C. Raykar, Linda H . Zhao, "Nonparametric prior for adaptive sparsity", Siemens Healthcare, University of Pennsylvania, Presentation, AL & Statistics 2010, May 14, 2010, 1-20.

* cited by examiner

Algorithm 1 *Algorithm: Metric Learning by MatrixBoost*

Input: A set of feature vectors $X = [x_1 \ x_2 \ \cdots \ x_n]$,
The triplet set $\mathcal{T} = \{(i,j,k) \mid x_i \text{ is closer to } x_j \text{ than to } x_k\}$.
Initialize $D_1((i,j,k))$ (usually set to $1/m$ where $m$ is the total number of triplets).
repeat
    Learn the optimal weak hypothesis $h_t(x,y) : \mathcal{X} \times \mathcal{X} \to \mathcal{R}$ according to distribution $D_t$.
    Choose $\alpha_t \in \mathcal{R}$.
    Update distribution $$D_{t+1}((i,j,k)) = \frac{D_t((i,j,k)) \exp(\alpha_t(h_t(x_i, x_j) - h_t(x_i, x_k)))}{Z_t}$$

where $Z_t$ is a normalization factor (chosen so that $D_{t+1}$ is a distribution).
until Some convergence criterion is met.
Output the final model $H(\cdot,\cdot) = \sum_t \alpha_t h_t(\cdot,\cdot)$.

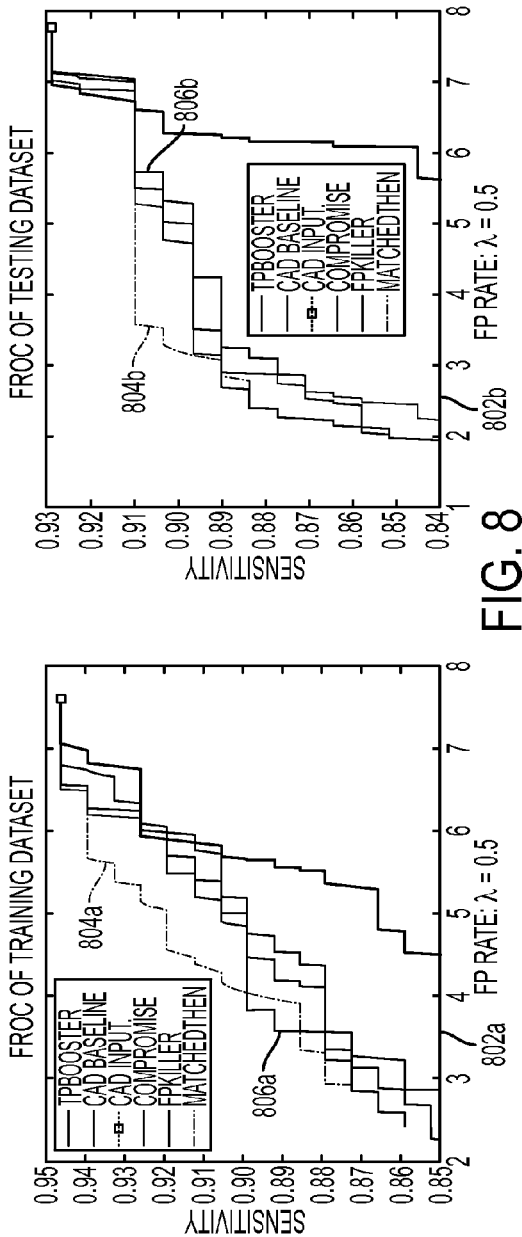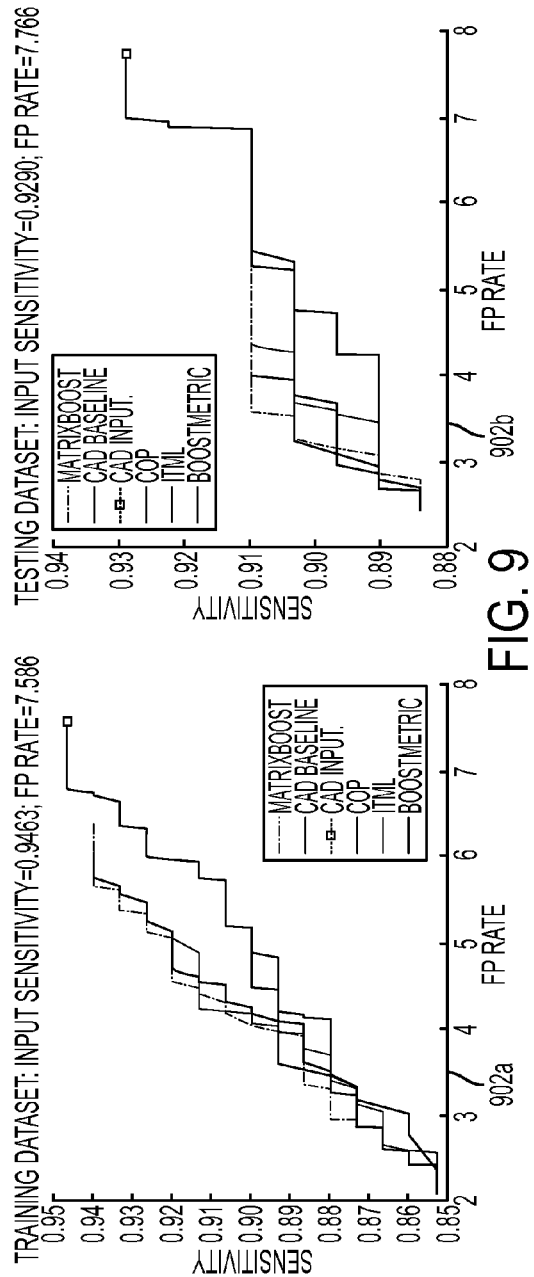
FIG. 8
FIG. 9

MATCHING OF REGIONS OF INTEREST ACROSS MULTIPLE VIEWS

CROSS-REFERENCE TO RELATED APPLICATION

The present application claims the benefit of U.S. provisional application No. 61/390,646 filed Oct. 7, 2010, the entire contents of which are herein incorporated by reference.

TECHNICAL FIELD

The present disclosure generally relates to processing of image data, and more specifically, to matching of regions of interest across multiple views.

BACKGROUND

The field of medical imaging has seen significant advances since the time X-Rays were first used to determine anatomical abnormalities. Medical imaging hardware has progressed in the form of newer machines such as Medical Resonance Imaging (MRI) scanners, Computed Axial Tomography (CAT) scanners, etc. Because of large amount of image data generated by such modern medical scanners, there has been and remains a need for developing image processing techniques that can automate some or all of the processes to determine the presence of anatomical abnormalities in scanned medical images.

Digital medical images are constructed using raw image data obtained from a scanner, for example, a CAT scanner, MRI, etc. Digital medical images are typically either a two-dimensional ("2-D") image made of pixel elements or a three-dimensional ("3-D") image made of volume elements ("voxels"). Such 2-D or 3-D images are processed using medical image recognition techniques to determine the presence of anatomical structures such as cysts, tumors, polyps, etc. Given the amount of image data generated by any given image scan; it is preferable that an automatic technique should point out anatomical features in the selected regions of an image to a doctor for further diagnosis of any disease or condition. Automatic image processing and recognition of structures within a medical image is generally referred to as Computer-Aided Detection (CAD). A CAD system can process medical images and identify anatomical structures including possible abnormalities for further review. Such possible abnormalities are often called candidates and are considered to be generated by the CAD system based upon the medical images.

CAD techniques have emerged as powerful tools for detecting colonic polyps in three-dimensional (3D) Computed Tomography Colonography (CTC) or virtual colonoscopy. 3D CTC is a noninvasive and effective tool for early detection of polyps, which are growths or bumps on the colorectal lining that usually indicate the presence of colon cancer. Colon cancer is the second leading cause of cancer death in western countries, but it is one of the most preventable of cancers because doctors can identify and remove its precursor known as a polyp. To enhance polyp findings in collapsed or fluid-tagged colon segments, and better distinguish polyps from pseudo polyps (e.g. tagged stools), the current CTC practice is to obtain two scans of a patient in prone and supine positions respectively. This allows the radiologist to not only see areas that may not be visible in the other scan, but also to assess the mobility of a finding. Any true polyp will not move within the colon, whereas pseudo polyps tend to shift when the position of the patient is changed. However, the colon can move and deform significantly between the prone and supine scans, which makes it difficult to assess whether a polyp or pseudo polyp has moved within the colon. Manual registration of polyp findings or colon segments is also difficult, inaccurate and time-consuming.

It is crucial that a polyp detection system and method have high sensitivity to true polyps. At the same time, it is extremely beneficial if the detection system minimizes the number of false positives detected. The ultimate goal is a system that can detect 100% of all malignant polyps (100% sensitive) while detecting zero false positive polyps. Current systems can reach approximately 88.9% sensitivity with 3.81 false positive (FP) rate per patient during CAD polyp detection. While these detection rates are a marked improvement over older systems, the less than 100% sensitivity and the moderate number of false positives detected still present a significant problem in providing sufficient early detection.

Therefore, there is a need for improved systems and methods for detecting polyps with maximum sensitivity and minimum false positives, and for assessing polyps by helping the radiologist to identify corresponding CAD findings across various views.

SUMMARY

The present disclosure relates to multi-view matching of regions of interest in images. According to one aspect of the disclosure, a processor receives first and second digitized images, as well as at least one CAD finding corresponding to a detected region of interest in the first image. The processor determines at least one candidate location in the second image that matches the CAD finding in the first image. The matching is performed based on local appearance features extracted for the CAD finding and the candidate location.

In accordance with another aspect, the processor receives digitized training images representative of at least first and second views of one or more regions of interest. Feature selection is performed based on the training images to select a subset of relevant local appearance features to represent instances in the first and second views. A distance metric is then learned based on the subset of local appearance features. The distance metric may be used to perform matching of the regions of interest.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

FIG. 4 shows an exemplary metric boosting method;

FIG. 8 shows comparative graphs illustrating results according to various aspects of the present disclosure; and FIG. 9 shows comparative graphs illustrating FROC performance according to one aspect of the present disclosure relative to other methods.

DETAILED DESCRIPTION

Figure 1:
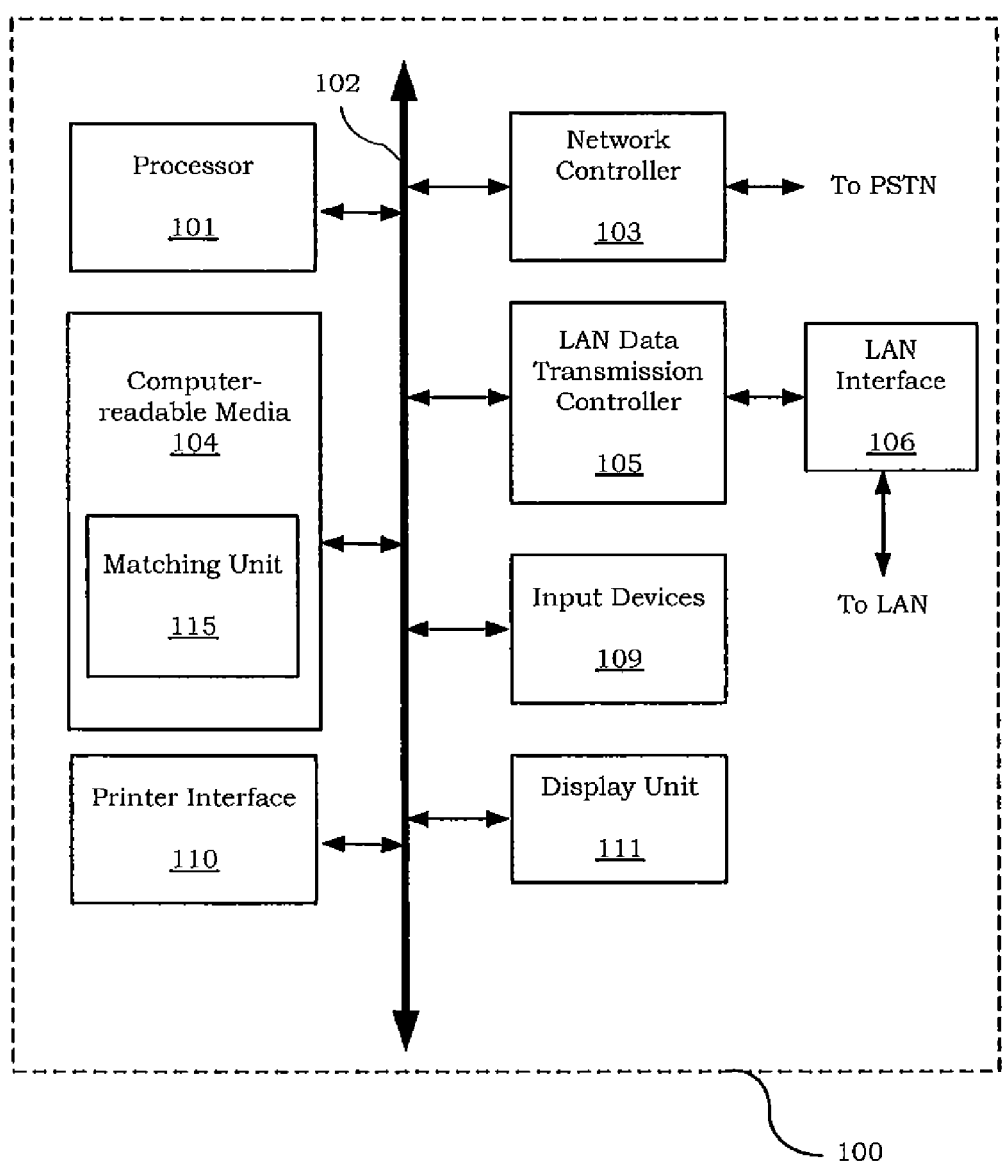
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary 3D imaging modality. It will be appreciated that data from any type of 3D imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulate and transform data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2D images and voxels for 3D images). The image may be, for example, a medical image of a subject collected by computed tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

In the following description, for purposes of explanation, specific numbers, materials and configurations are set forth in order to provide a thorough understanding of the present frameworks and methods and in order to meet statutory written description, enablement, and best-mode requirements. However, it will be apparent to one skilled in the art that the present frameworks and methods may be practiced without the specific exemplary details. In other instances, well-known features are omitted or simplified to clarify the description of the exemplary implementations of present frameworks and methods, and to thereby better explain the present frameworks and methods. Furthermore, for ease of understanding, certain method steps are delineated as separate steps; however, these separately delineated steps should not be construed as necessarily order dependent in their performance.

It is to be understood that embodiments of the present invention can be implemented in various forms of hardware, software, firmware, special purpose processes, or a combination thereof. In one embodiment, the present technology can be implemented in software as an application program tangibly embodied on a non-transitory computer readable medium. The application program can be uploaded to, and executed by, a machine comprising any suitable architecture. The system and method of the present disclosure may be implemented in the form of a software application miming on a computer system, for example, a laptop, personal computer (PC), workstation, client device, mini-computer, storage system, handheld computer, server, mainframe computer, dedicated digital appliance, and so forth. The software application may be stored on a non-transitory recording media locally accessible by the computer system and accessible via a hard wired or wireless connection to a network, for example, a local area network, or the Internet.

The following description sets forth one or more implementations of systems and methods for facilitating multi-view matching of regions of interest in images. One aspect of the present disclosure is to find a match for each candidate instance by using a distance metric (or similarity metric). If a match can be found, then the candidate instance will be detected as a positive instance (e.g., true polyp). Otherwise, if a match cannot be found and the CAD classification score (which measures the probability for a candidate to be a true positive (TP)) for the candidate is low (i.e. below a predetermined score threshold), then the candidate instance will be detected as a negative instance (e.g., false polyp). A match may be identified if the distance between a pair of instances is below a predetermined distance threshold. For example, true pairs of polyp detections have smaller distances (or larger similarities) than false pairs. To find the distance between two candidate instances, the systems and methods of the present disclosure may learn a distance (or similarity) metric.

In one implementation, the present framework performs supervised learning of a distance metric in the feature space of classification, where true pairs of candidate instances statistically have smaller distances (or larger similarities) than false pairs of candidate instances. The feature space of classification includes multiple local appearance features representing each instance. Since the combination of these features may lead to redundancy, greater computational and spatial complexity, feature selection may first be performed to choose the features that are most relevant to the task of matching and/or ranking (e.g., the feature variation is minimal between truly matched polyps), but least redundant. After pruning and selecting task-specific features from the original classification feature pool, an efficient metric boosting method may be performed to learn a boosted distance metric from the subset of selected features to measure the difference between instances. Other types of metric learning methods may also be used.

One aspect of the present framework uses only local appearance features to learn a matching distance metric. Previous work is based on global geometric information, and generally involves indexing polyp or lesion findings according to their normalized geometric coordinates along the geodesic curve tracing from rectum (0) to cecum (1) within colon lumen. In contrast, one aspect of the present framework uses local polyp classification features extracted from a local ROI centered at each candidate to build pair-wise matching functions. Since only local features are used, the present framework can seamlessly handle collapsed colon segments or other severe structural artifacts which often exist in CTC, whereas other global geometry dependent methods may become invalid for collapsed segmentation cases. Unlike conventional techniques that require completely distended colon segmentation, no global centerline or surface extraction and registration are required, thereby avoiding the challenges posed by collapsed or deformed colon segments that occur frequently in daily clinical practice.

The framework described herein may be used to achieve high performance in, for example, polyp prone-supine view matching to facilitate the regular CTC workflow where radiologists need to manually match the computer-aided detection (CAD) findings (or annotation markers) in prone and supine image scans for validation. The present framework greatly facilitates current clinical polyp cross-view matching workflow with excellent accuracy. The process of matching polyp findings in prone-supine scans increases radiologists' confidence in polyp detection, because it facilitates the identification of moving false-positives (FPs) while retaining true-positives (TPs). It is believed that the present local appearance matching approach brings automatic polyp matching one step closer to clinical practice. Additionally, no or little extra computation overhead is imposed, compared to the additional computing expenses incurred in conventional techniques due to surface registration, centerline extraction and matching. The present framework significantly outperformed conventional polyp matching methods, leading with a large margin evaluated on at least one order-of-magnitude larger multiple hospital datasets. Even further, hundreds of cases in multi-site clinical datasets may be processed, without manual editing of noisy colon segmentations, which makes it convenient for automatic large scale evaluation.

It is understood that while a particular application directed to prone-supine view matching and classification of polyps may be shown, the technology is not limited to the specific embodiments illustrated. For example, the present technology has application to other types of anatomical structures, such as matching breast cancer lesions in mammograms, and matching polyps or lung nodules in 2D/3D medical images at different time points for follow-ups.

FIG. 1 shows an example of a computer system which may implement a method and system of the present disclosure. The computer system referred to generally as system 100 may include, inter alia, a processor 101, a non-transitory computer readable media 104, a printer interface 110, a display unit 111, a local area network (LAN) data transmission controller 105, a LAN interface 106, a network controller 103, an internal bus 102, and one or more input devices 109, for example, a keyboard, mouse, tablet, touch-screen etc.

The non-transitory computer-readable media 104 can include random access memory (RAM), read only memory (ROM), magnetic floppy disk, disk drive, tape drive, flash memory, etc., or a combination thereof. The present framework may be implemented as a matching unit 115 that includes computer-readable program code tangibly embodied in the non-transitory computer-readable media 104 and executed by the CPU 101. As such, the computer system 100 is a general purpose computer system that becomes a specific purpose computer system when executing the routine of the present invention. The computer-readable program code is not intended to be limited to any particular programming language and implementation thereof. It will be appreciated that a variety of programming languages and coding thereof may be used to implement the teachings of the disclosure contained herein.

The system 100 may also include an operating system and micro instruction code. The various processes and functions described herein can either be part of the micro instruction code or part of the application program or routine (or combination thereof) which is executed via the operating system. In addition, various other peripheral devices, such as an additional data storage device, a printing device and an imaging device, can also be connected to the computer platform. The imaging device may be, for example, a radiology scanner such as a magnetic resonance (MR) scanner or a computed tomographic (CT) scanner. The matching unit 115 may be executed by the CPU 101 to process digital image data (e.g., MR or CT images) from the imaging device.

It is to be further understood that, because some of the constituent system components and method steps depicted in the accompanying figures can be implemented in software, the actual connections between the systems components (or the process steps) may differ depending upon the manner in which the present framework is programmed. Given the teachings of the present framework provided herein, one of ordinary skill in the related art will be able to contemplate these and similar implementations or configurations of the present framework.

Figure 2:
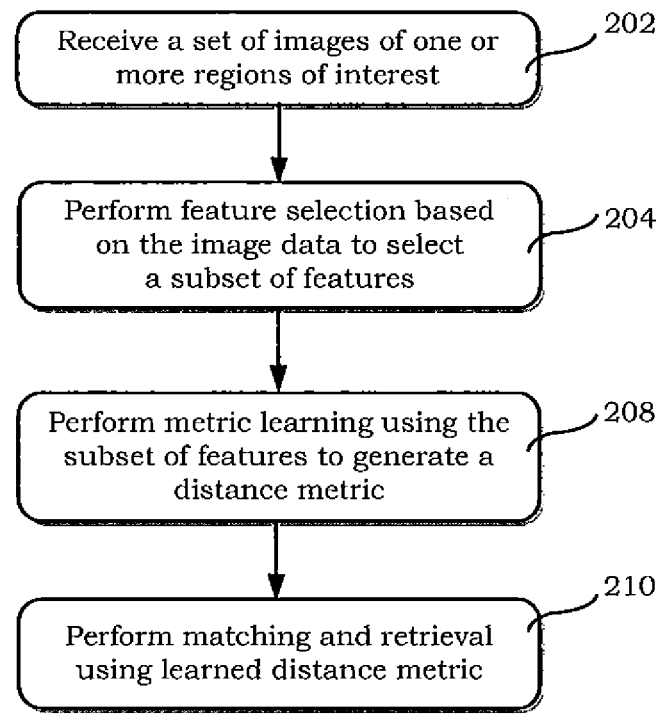
FIG. 2 shows an exemplary method of matching images.

FIG. 2 shows an exemplary method 200 of matching images in accordance with one implementation of the present framework. The steps of the method 200 may be performed in the order shown or a different order. Additional, different, or fewer steps may be provided. The exemplary method 200 may be implemented by the matching unit 115 in the computer system 100, which has been previously described with reference to FIG. 1, a different system or a combination thereof.

At 202, the matching unit 115 receives a set of images of one or more regions of interest (ROIs). The images comprise, for example, two-dimensional (2-D) cross-sectional images or three-dimensional (3-D) volumetric image data reconstructed from acquired cross-sectional slice images. The images may be acquired by an imaging device using magnetic resonance (MR) imaging, computed tomography (CT), helical CT, x-ray, positron emission tomography, fluoroscopy, ultrasound or single photon emission computed tomography (SPECT). Other types of imaging modalities may also be used. The images may also be acquired by different modalities. For example, the images may comprise multiple image data sets acquired with MR, CT, PET, and SPECT scanners. Different modalities may be used because each modality provides special information not available in other modalities. Additionally, in CTC cases, the images may be acquired with fecal tagging preparation to improve the differentiation of residual feces from polyps, thereby avoiding or minimizing false-positive candidates.

The images may be collected from different patients. In addition, the images may be retrieved from a training dataset for learning the distance metric, and/or a testing dataset for validating the learned distance metric. For example, the training dataset may include 195 CTC cases (or 390 volumes) with 106 polyps appearing in both views, while the testing dataset may include 223 CTC cases containing 118 polyps with double appearance, collected from 8 hospitals in US, Europe and Asia.

In addition, the images may include one or more regions of interest (ROIs). A region of interest (ROI) is any area in the image data that has been identified for further study and examination (e.g., a colonic segment or any other structure of a patient). A detected ROI may be graphically annotated with computer-aided detection (CAD) markers. A CAD marker is associated with a CAD finding (or detection), which may be automatically provided by a CAD algorithm or manually provided by a skilled user (e.g., radiologist). A CAD finding is a location in the medical image that has been identified as warranting additional study and examination. A CAD algorithm usually identifies a preliminary set of candidate findings in a medical image, and then selects which ones, if any, will qualify as actual CAD findings based on a variety of computed features associated with the candidate findings.

In one implementation, the images are representative of one or more candidate abnormalities in the ROI. A candidate abnormality may be a suspicious structure, such as a polyp, lung nodule, liver tumor, breast cancer lesion, prostate cancer tumor, etc. In addition, the candidate abnormalities may be represented in a variety of 2D or 3D images across different views. The different views include prone, supine, lateral and/or decubitus views of the patient. For example, the images may correspond to a plurality of CTC cases (or volumes) with a plurality of polyps appearing in both supine and prone views. Alternatively, the different views may refer to views of the same subject acquired at different times.

Each view of each subject (or patient) corresponds to an image volume. A unique volume ID may be provided for each volume, and a unique patient ID provided for each subject. There may be a number of candidate instances (e.g., polyp candidates) in each volume, where some are positive (or true) instances, and some are negative (or false) instances. Several positive instances may refer to one candidate abnormality (e.g., polyp) and thus have the same abnormality ID. Also, one candidate abnormality may appear in two different views or different times. In one implementation, only actionable candidate structures with diameters greater than a predetermined value (e.g., 6 mm) are considered.

The images may be represented as follows: $x_i^1$ denotes a true polyp instance in a first view (e.g., prone view) of a patient, and $\{x_j^2\}$ denotes the set of corresponding instances in a second view (e.g., supine view). The size of $\{x_j^2\}$ may be larger than one, since polyps can appear as two or more instances in each scan, especially for large polyps. This is called a multiple instance problem. The instances in the two views rooted from the same unique true polyp are defined as positive (or true) pairs, while other pairs are defined as negative (or false) pairs (e.g., TP-TP pairs according to different polyps, TP-FP pairs, and FP-FP pairs).

Each instance (or candidate abnormality) may have multiple local features represented by a multidimensional vector. The local features may be identified by experts or automatic algorithms. The local features may include appearance features, such as intensity, shape, texture-based, geometrical or contextual features (e.g., world or volume coordinates). It should be understood that other types of local features may also be used. As discussed previously, unlike previous work that is based on global geodesic coordinates, the present implementation uses local features to capture local observations for finding matches. This advantageously provides the ability to handle collapsed CTC cases with superior robustness. For each original feature f, a new "difference-of-feature" variable can be derived as $\Delta f = (f_i^1 - f_j^2)$, which is expected to be zero or a constant for positive pair population (i.e., tightly distributed in a more general statistical sense), or random for negatives.

In order to reduce computational costs, the image data may be pre-processed to rule out (or exclude) false-positive (FP) candidate instances. In one implementation, a classifier is constructed, based on the features, and used to perform a thresholding process to rule out FP candidates with low probabilities ($\rho$) of being the anatomical structure (e.g., polyp). For example, a tree-structured probabilistic classifier may be used to process 61,257 candidates with 96 features $F = \{f_i\}$ to obtain about 8 candidates per patient with TP detection sensitivities at 94.2% and 92.9% for training and testing respectively.

At 204, the matching unit 115 performs feature selection based on the images to select a subset of features (S). Since the total union of features based on the images may lead to redundancy, greater computational and spatial complexity, feature selection is performed at 204 to choose the features that are most relevant to polyp matching and/or ranking (e.g., where feature difference variation, as a new random variable, is minimal between true polyp matches), but least redundant. After feature selection, the number of features for each candidate may be reduced from, for example, 96 to 20. Any suitable feature selection technique, such as Bayesian feature selection, correlation feature selection, local learning based feature selection, Minimum Redundancy Maximum Relevance (MRMR) method, etc., may be used to select a subset of features (S) from the entire CAD classification feature pool ($\Im$). See, e.g., Peng, H., Long, F., Ding, C., "Feature Selection Based on Mutual Information: Criteria of Max-dependency, Max-relevance, and Min-redundancy," IEEE TPAMI (2005) 1226-1238, which is herein incorporated by reference for all purposes.

In one implementation, the MRMR method is used for feature selection. For feature set $\Im = \{f_i\}$, the MRMR feature subset S means that the average mutual information between the feature set S and the class labels is large, while the mutual information between the features in S is small. The mutual information between feature set S and the class label set y may be defined as:

$$I(S, y) = \frac{1}{m} \sum_{f_i \in S} I(f_i, y) \quad (1)$$

where in is the cardinality of S, I is the mutual information and y represents the positive/negative {+1; −1} matched pair as defined previously. The mutual information between features in the set S may be defined as:

$$I(S) = \frac{1}{m^2} \sum_{f_i, f_j \in S} I(f_i, f_j) \quad (2)$$

The objective of the MRMR method may be described by the following function:

$$\gamma(S, y) = \max_{S \subset \mathcal{I}} I(S, y) - I(S) \quad (3)$$

In one implementation, the MRMR feature selection is a sequential process. The $i^{th}$ feature $f^*_i$ may be selected, given the selected $S_{i-1}$, according to the following equation:

$$f_i^* = \arg\max_{f \in \mathcal{I} - S_{i-1}} I(f, y) - \frac{1}{i-1} \sum_{f_j \in S_{i-1}} I(f, f_j) \quad (4)$$

Figure 3:
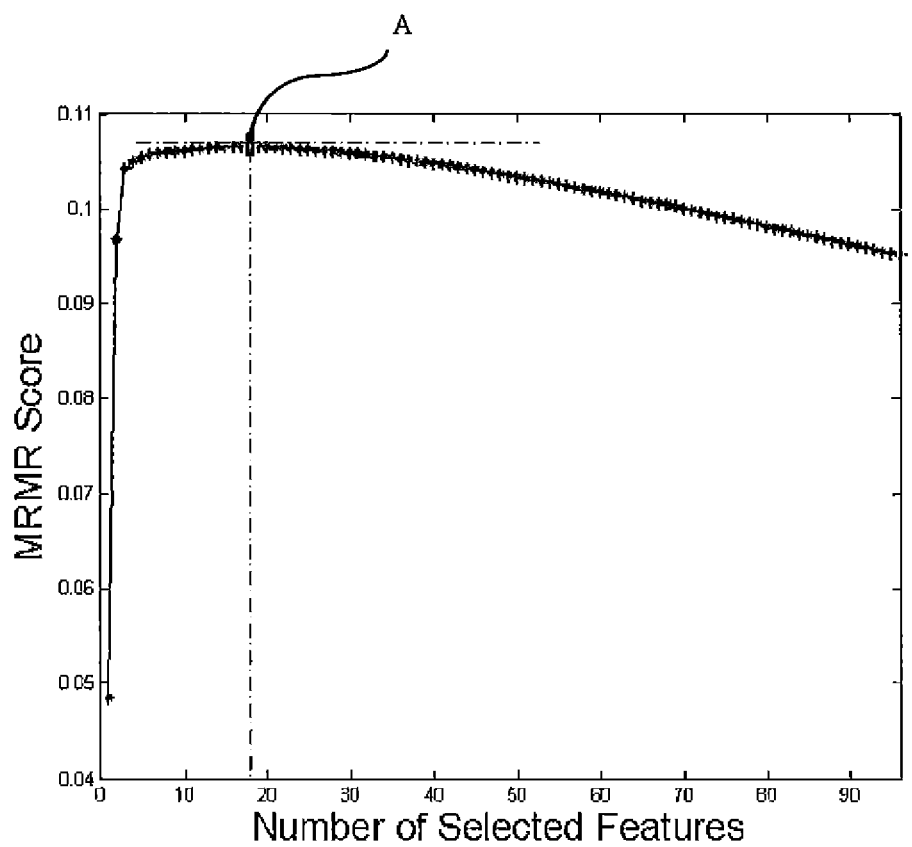
FIG. 3 shows an exemplary graph of the Minimum Redundancy Maximum Relevance (MRMR) score versus number of features selected.

The $i^{th}$ feature may be added to $S_{i-1}$ to form $S_i = S_{i-1} \cup f_i$. If $\gamma(S_i, y) < \gamma(S_{i-1}, y)$, then $S_{i-1}$ is the optimal feature subset, and the MRMR feature selection terminates. FIG. 3 shows an exemplary graph of the MRMR score versus the number of features selected. As shown by point A, the maximum MRMR score is achieved when a subset of 18 features is selected from a set of 96 features.

At 208, the matching unit 115 performs metric learning using the selected subset of features to generate a distance (or similarity) metric. In one implementation, metric boosting ("MatrixBoost") is used to learn an effective matching distance metric (or decision). It should be noted, however, that other types of metric learning techniques (e.g., Mahalanobis, PSDBoost, Information-Theoretic Metric Learning, Boost-Metric, COP) may also be used to learn the distance metric. See, e.g., Xing, E., Ng, A., Jordan, M., Russell, S., "Distance Metric Learning, with Application to Clustering with Side-information," NIPS 15 (2002) 505-512; Bar-Hillel, A., Hertz, T., Shental, N., Weinshall, D., "Learning a Mahalanobis Metric from Equivalence Constraints," J. Mach. Learn. Res. 6 (2005) 937-965; Shen, C., Kim, J., Wang, L., van den Hengel, A., "Positive Semidefinite Metric Learning with Boosting," NIPS (2009) 1651-1659; Davis, J., Kulis, B., Jain, P., Sra, S., Dhillon, I. S., "Information-Theoretic Metric Learning," ICML (2007) 209-216, which are all herein incorporated by reference.

The learned distance metric should provide smaller values for a true pair of matching positive instances of a polyp in the prone-supine views than a false (or non-matching) pair. The distance metric may be designed to match, for example, polyp instances in the different views. Other types of matching tasks may also be performed. A good distance metric should be robust, consistent and automatically put more weight on better (i.e. more representative and intrinsic) features and less weight on worse features in the feature space. In other words, low distances should be given to pairs of instances to be matched, while high distances should be given for others. A well-designed distance metric can greatly enhance performance. For tasks with high-dimensional data with redundant and irrelevant features, sparse distance metrics based on fewer features become desirable. See, e.g., Jinbo Bi, Dijia Wu, Le Lu, Meizhu Liu, Yimo Tao, Matthias Wolf, "AdaBoost on Low-Rank PSD Matrices for Metric Learning with Applications in Computer Aided Diagnosis," CVPR'2011: IEEE Conference on Computer Vision and Pattern Recognition, June 2011, Colorado Springs, USA, which is herein incorporated by reference.

The goal of metric learning is to learn a distance function d such that $d(x_i, x_j) < d(x_i, x_k)$. For each true positive instance (e.g., polyp) $x_i$ in the first view (e.g., prone view of a patient), $\{x_j\}_{j=1}^n$ represents all the positive instances corresponding to the same polyp, and $\{x_k\}_{k=1}^m$ represents all other instances, including positives corresponding to different polyps and negatives, or false positives, in the second view (e.g., supine view). In one implementation, a proximity preserving approach is used to learn a Mahalanobis distance metric, which is parameterized by a positive semi-definite (PSD) matrix M. The Mahalanobis distance between 2 instances $x_i$ and $x_j$ may be defined as:

$$d(x_i, x_j) = (x_i - x_j)' M (x_i - x_j) \quad (5)$$

where ' is the vector/matrix transpose transformation, M is a positive semi-definite (PSD) matrix that leads to the Mahalanobis distance metric and $x_i$ and $x_j$ are vectors in $R^d$. The PSD matrix M preserves the proximity relationships among triplet set T={(i j, k)}. It should be understood that other types of distance metrics, such as multidimensional scaling (MDS) and locally linear embedding (LLE) may also be used.

Metric boosting may be performed by optimally combining weak learners to form a strong learner, based on the image data. One type of weak learner is equivalence constrained, where equivalence constraints are provided for pairs $(x_i, x_j)$, each of which is associated with a binary label of "similar" or "dissimilar." Another type of weak learner representation is constrained by the proximity relationship over triplet set T={ (i, j, k)}, wherein $x_i$ is closer to $x_j$ than to $x_k$. The triplet sets T may be constructed based on instances with classifier score (ρ) greater than a predetermined score threshold ($\beta_c$). The predetermined score threshold is selected to make a practically feasible compromise between detection sensitivity and FP rate (e.g., $\beta_c$=0.0157, sensitivity=0.9463 and FP=7.586). Once the instances are selected, they can be used to form the triplets. The triplets may be used as input to the metric boosting step 208 for learning.

A triplet may be formed by (i, j, k), constrained by the distance inequality relationship: $d(x_i, x_j) < d(x_i, x_k)$, where d denotes the metric distance. Abstractly speaking, the intra-polyp difference should be smaller than the inter-polyp difference, as well as the difference between polyps and false polyps. Once the distance metric satisfies these constraints, systems and methods of the present disclosure can use the metric to find matches (or closest neighbors) for each candidate, and if a match is found, it means this candidate has a high probability of being a polyp. The same process may be repeated for each true positive instance in the second view (e.g., supine view) to build more triplets in a similar way. All the triplets form a triplet set T including, for example, 8646 triplets in total.

As discussed previously, the Mahalanobis distance is defined based on the PSD matrix M in accordance with Equation (5). Since the PSD matrix M is greater than or equal to zero, it can be Eigen-decomposed into lower rank PSD matrices (e.g., $M=\alpha_i U_i$, where $U_i=u_i u_i'$). Certain aspects of the present framework constructs the PSD (or "covariance") matrix M by additively combining weak learners that are low rank PSD matrices. The AdaBoost method may be used to learn the linear combination of low rank PSD matrices, as a PSD matrix M preserving the proximity relationships among triplet set $T=\{(i, j, k)\}$. Different options of weak models and combination coefficients may lead to different metric learning algorithms. The distance between two instances $x_i$ and $x_j$ is $d(x_i, x_j)=(x_i-x_j)'M(x_i-x_j)$. A strong learner $H(x, y)=(x-y)'M(x-y)$ can be learned by combining learners $h_t(x, y)=(x-y)'U_t(x-y)$, i.e. $H(x, y)=\Sigma_t \alpha_t h_t(x, y)$, which can minimize the error rate ($\square$) of triplets violating the distance inequality.

$$\epsilon = \sum_{(i,j,k)\in T} D((i, j, k)) 1_{(H(x_i,x_j)-H(x_i,x_k))} \quad (6)$$

where D is a probability distribution over T, and 1 is the Heaviside step function ($1_{(a)}=0$ if $a<0$, and 1 otherwise).

According to aspects of the present disclosure, the system may learn the PSD matrix M using metric boosting. FIG. 4 shows an exemplary metric boosting method 400. The method 400 adapts the merits of the AdaBoost method and the decomposable nature of the PSD distance matrix. The weak model may be, for example, $h_t(x, y)=(x-y)'U_t(x-y)$ where $U_t=u_t u_t'$. The final hypothesis is $H(x, y)=(x-y)'M(x-y)$ where $M=\Sigma_t \alpha_t U_t$. It should be noted that if M forms a metric that satisfies the triplet conditions, so does its multiplier. It can be proven that the training error of the final hypothesis H as defined in (6) is upper bounded by $\Pi_{t=1}^T Z_t$, i.e., $$\sum D((i, j, k)) 1_{(H(x_1,x_j)-H(x_i,x_k))} \le \sum D((i, j, k,)) \exp\left(\frac{H(x_i, x_j)-}{H(x_i, x_k)}\right), \quad (7)$$

$$1_x \le \exp(x)$$

$$= \sum D_{T+1}((i, j, k)) \prod_{t=1}^T Z_t$$

$$= \prod_{t=1}^T Z_t.$$

$\alpha_t$ and $h_t$ may be chosen such that the error upper bound $\Pi_{t=1}^T Z_t$ will be minimized. Various definitions of $h_t$ may be applied. For example, $h_t \in [0, \infty]$, $h_t \in \{0, 1\}$, or $h_t \in [0,1]$. Assuming $h_t \in [0, 1]$, then for any real value of $\alpha_t$, $Z_t$ has the upper bound:

$$Z_t \le e^{\alpha_t}\frac{1-r}{2} + e^{-\alpha_t}\frac{1+r}{2} \quad (8)$$

where $$r = \sum_{(i,j,k)\in T} D_t((i, j, k)) 1_{(h_t(x_i,x_k)-h_t(x_i,x_j))} \quad (9)$$

The right side of Equation (8) can be minimized when $\alpha_t=\ln((1+r)/(1-r))/2$, which corresponds to $Z_t \le \sqrt{1-r^2}$. Since $Z_t \le 1$, if $r>0$, $\alpha_t>0$. In addition, the inequality implies that a smaller $Z_t$ may be achieved by minimizing its upper bound $\sqrt{1-r^2}$. Hence, a weak learner may be designed to maximize $|r|$ for a sensible model $h_t$.

$$\max_{U_t=u_t u_t'} \left|\sum_{(i,j,k)\in T} D_t((i, j, k))(h_t(x_i, x_k) - h_t(x_i, x_j))\right| \quad (10)$$

$$\|u_t\| = 1$$

subject to $h_t(x, y) = (x - y)'U_t(x - y)$

Using simple matrix algebraic operations, Equation (10) may be rewritten as:

$$\left|u_t'\left[\sum_{(i,j,k)\in T} D_t((i, j, k))((x_i - x_k)(x_i - x_k)' - (x_i - x_j)(x_i - x_j)')\right]u_t\right| \quad (11)$$

The problem of maximizing the objective function (11) subject to a normalization constraint $\|u_t\|=1$ has a closed-form solution: the optimal $u_t$ is the eigenvector corresponding to the eigenvalue $\lambda$, which has the largest absolute value, of the matrix $$\Sigma_{(i,j,k)\in T} D_t((i,j,k))((x_i-x_k(x_i-x_k)'-(x_i-x_j)(x_i-x_j)') \quad (12)$$

Let $a=\max\{\|x-y\|\mid x \ne y, x,y \in X\}$, which is a constant for a given set of data.

$$0 \le h_t(x, y) = \frac{(x-y)'u_t u_t'(x-y)}{a^2} \le \frac{\|x-y\|^2 \|u_t\|^2}{a^2} \le 1 \quad (13)$$

During testing, if $d(x_i, x_k)<\delta$ where $\delta$ is a distance threshold which can be statistically calibrated as shown later, $x_k$ may be claimed as a match of $x_i$ and the confidence $p_i$ for $x_i$ to be detected as positive (assuming only true positives have matches) is inverse to the minimum distance, i.e., $p_i=1/d(x_i, x_k)$. Existing mathematical programming-based metric learning algorithm requires a computation cost in the order of $|T|$, wherein $|T|$ is the cardinality of the triplet set T, which is very computationally expensive and not well scalable, since a large number of triplets are needed to learn a proper metric for most applications. Unlike conventional techniques, the present framework leverages efficient boosting optimization and decomposes triplet constraints into pairs and directly works on the pairs, which is about 4 to 10 times faster than conventional techniques. In addition, the present framework does not require any tuning parameters to specify via cross validation.

Figure 5A:
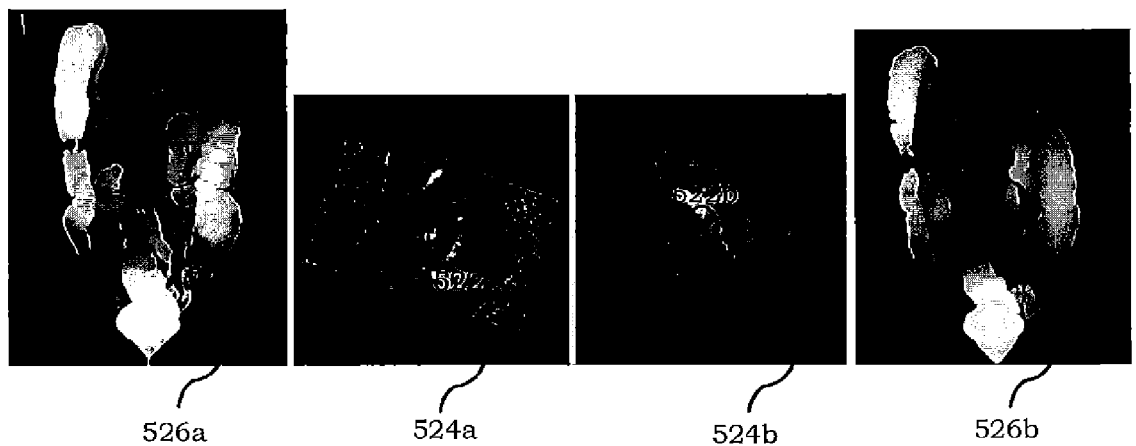
FIG. 5a shows an exemplary matched polyp pair.

Referring back to FIG. 2, at 210, the matching unit 115 performs matching and/or retrieval by using the learned distance metric. The present framework presents a robust and efficient method of matching two or more ROIs by searching for local regions that meet certain similarity or distance criteria, instead of computing the displacement field and transformation of the entire image. The goal of retrieval is to automatically determine a matching candidate instance (or location or region) of the same anatomical abnormality in another image. For example, given a lesion in a first image, the goal may be to find a region in a second image that looks similar to the lesion. The matching unit 115 extracts local appearance features, characteristics or properties for the lesion in the first image and then searches for regions in the second image that have similar characteristics. FIG. 5a shows an exemplary polyp pair matched by the present framework.

The polyps 522*a-b* in images 524*a-b* are successfully matched, despite being in a collapsed colon with background topological noise (e.g., small intestine) and large deformations in traverse and ascending colon sections, as shown in images 526*a-b*.

The present framework may also be used to make decisions on whether a candidate instance is a positive candidate (e.g., polyp) by integrating the matching function with the CAD classification framework. Such integration can greatly improve the CAD performance by reducing the number of false positives and increasing the sensitivity of polyp detection tremendously at small FP rate. Since true polyps do not move within the colon while other objects or false polyps (e.g., tagged stool) move within the colon when the patient changes position, false positives may be ruled out by matching polyps in different views (e.g., prone, supine, lateral or decubitus positions).

Figure 5B:
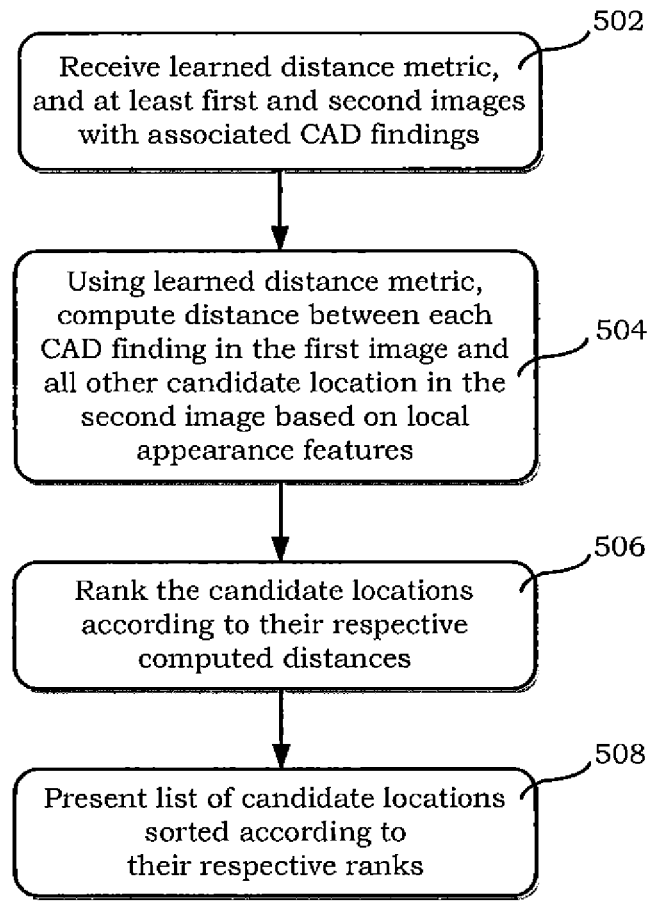
FIG. 5b shows an exemplary ranking method.

The retrieved candidate locations (or markers or findings) may be ranked according to the distances computed using the learned distance metric. FIG. 5*b* shows an exemplary ranking method in accordance with one implementation. At 502, the matching unit 115 receives the learned distance metric, and at least first and second images with one or more associated CAD findings (or markers). The first and second images may be acquired from the same patient by using the same or different modalities. The images may present an candidate abnormality (e.g., polyp or lesion) in different views (e.g., prone or supine views). The one or more CAD findings correspond to one or more ROIs detected in at least the first image. A set of CAD findings (or markers) may also be provided for the second image. The one or more ROIs may be detected manually by a user, or automatically by a CAD algorithm.

At 504, the learned distance metric is used to compute the distance in feature space between each CAD finding in the first image and candidate locations in the second image. For each CAD finding $x_i$ in the first image, the matching unit 115 automatically extracts the local appearance features of the region of interest associated with the CAD finding $x_i$. Using the extracted local appearance features, the distance $d(x_i, x_j)$ between the CAD finding $x_i$ in the first image and a candidate location $x_j$ in the second image using Eq. (5) based on the learned matrix M. If one or more CAD findings are provided for the second image, the candidate location will be at one of the CAD findings in the second image. Otherwise, candidate markers may be generated in the second image and matched with each CAD finding in the first image.

At 506, the candidate locations are ranked according to their respective computed distances d. The matching unit 115 may select the k nearest neighbors having the smallest distance difference with the CAD finding $x_i$ in the first image. The k nearest neighbors are sorted and checked to determine whether there is a true match within k to trigger a 'hit'. In case of multiple instances, any true instance appearing in the top k neighbors will count the candidate abnormality as retrieved at k. The retrieval rate, defined as the number of hits divided by the number of candidate abnormalities, may be recorded. The retrieval rate may be evaluated based on the k nearest neighbors. Higher retrieval rates with smaller k will be helpful for doctors to detect candidate abnormalities.

At 508, the set of candidate locations in the second image may be sorted according to their respective ranks and presented in a sorted list. For example, the candidate locations may be sorted in ascending order, where candidate locations with smaller metric distances are presented first in the list. Other types of ordering, such as descending order, may also be presented. The sorted list may be presented by a display device via a user interface.

Figure 5C:
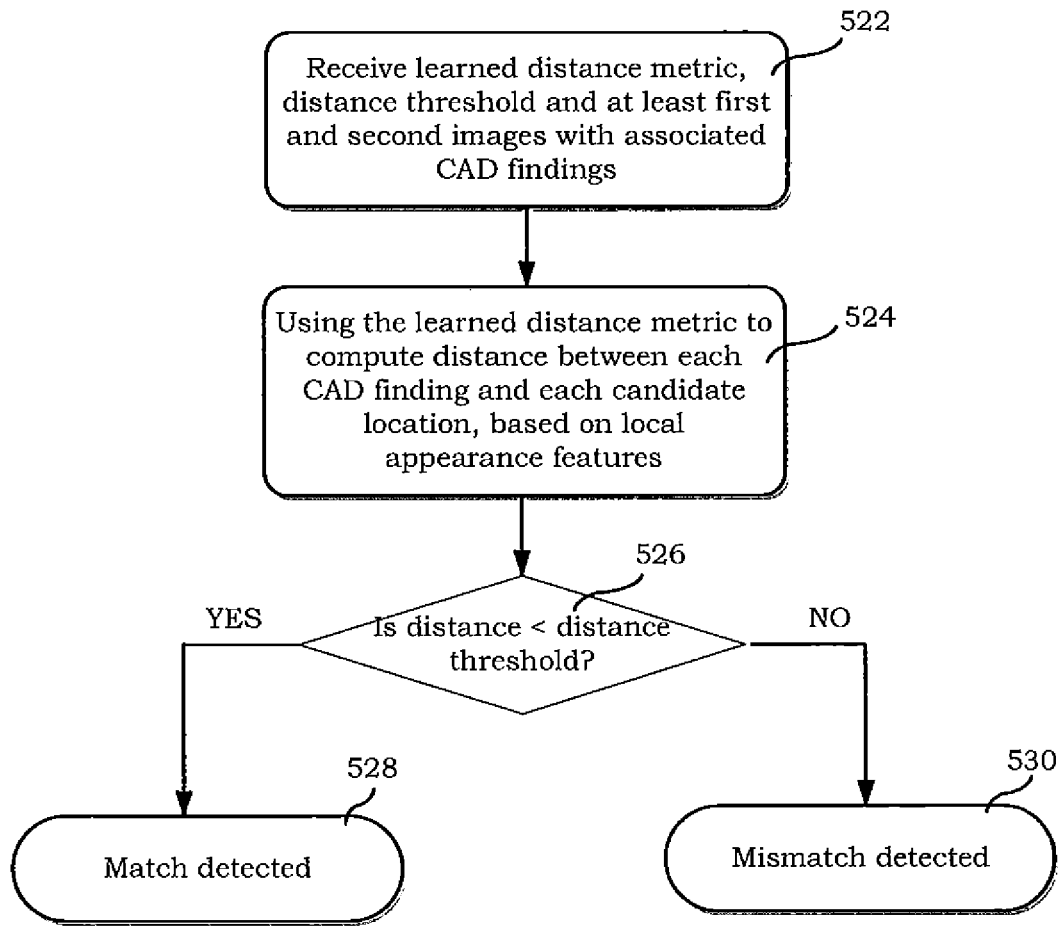
FIG. 5c shows an exemplary method of matching polyp candidates.

FIG. 5*c* illustrates an exemplary method 210 of determining whether a candidate is a polyp. At 522, the learned distance metric and a distance threshold is received, along with at least first and second images with associated CAD findings. One or more CAD findings in the first image correspond to one or more polyps. At 524, using the learned distance metric, the distance in feature space between each CAD finding in the first image and each candidate location in the second image is computed. Optionally, a relaxed Geodesic distance based filtering of instances can be enforced when available. If the distance is less than the distance threshold, a match is found at 528, and a positive candidate is detected. Otherwise, a mismatch is found at 530. A false candidate is detected if the classification score (determined by the CAD algorithm) of the candidate is below a score threshold.

Accordingly, a match is determined when the distance between the CAD finding and candidate location is below the distance threshold. The distance threshold may be initialized as the mean distance plus variance of all the ground truth matches (e.g., pairs of positives with the same polyp ID but in different views). The score threshold may be selected in the following exemplary way:

$$score_{threshold} = \underset{score}{\operatorname{argmax}} \ \text{sensitivity} \ (FP \ \text{rate} \leq 4) \quad (14)$$

The exemplary equation (14) indicates that most attention is paid to the points with false positive (FP) rate of no more than a predetermined rate of 4, while maximizing sensitivity. It should be understood that other FP rates may also be considered.

More particularly, the process of determining the score threshold may be statistically calibrated as follows: first, the initial score threshold is fixed, and the distance threshold varied to determine a Receiver Operating Characteristic (ROC) curve. The score threshold is then varied by a little, and another ROC curve is determined. The above process is then iteratively repeated for a predetermined number of times, and then the score threshold value is selected at the point of the ROC curve where the sensitivity is at its maximum value while maintaining the FP rate to be less than or equal to a predetermined rate of 4. It should be understood that different metrics will result in different ROC curves and thus different score thresholds.

In one implementation, one or more rule-based heuristics are used to integrate the above-mentioned matching or pairing techniques with classification routines to improve CAD performance. In accordance with one implementation, two split-tree classification rules of "if matched, accept; → else, validate" and "if non-matched, reject; → else, validate" are applied. For example, if a CAD finding $x_i$ finds a match with another candidate location $x_k$ such that the distance $d(x_i, x_k) < \delta$, then this pair of instances $(x_i, x_k)$ will be classified as positive; otherwise, the original CAD classification score ρ determines its class. The original CAD classification score ρ may be obtained from a CAD algorithm, and it measures the probability for the instance to belong to a given class (e.g., TP or FP). Any type of suitable CAD algorithm may be used. See, e.g., Vikas C. Raykar, Balaji Krishnapuram, Jinbo Bi, Murat Dundar, R. Bharat Rao, "Bayesian multiple instance learning: automatic feature selection and inductive transfer," The 25th International Conference on Machine Learning (ICML 2008): 808-815, which is herein incorporated by reference.

Each metric distance threshold ($\delta$) may invoke a Free-Response Operator Characteristic (FROC) curve on classification score $\rho$. An optimal $\delta$ may be chosen, giving the highest Area under Curve (AIX) of the FROC curves.

In another implementation, the original CAD classification scores ($\rho_{prone}$ and $\rho_{supine}$) of a pair of matched candidates in prone and supine scans are combined into a new classification score ($\rho_{prone}^{new}$ or $\rho_{supine}^{new}$). The combined single score ($\rho_{prone}^{new}$ or $\rho_{supine}^{n32}$) may be used to update both candidates in the respective pair. For example, the new classification scores ($\rho_{prone}^{new}$ and $\rho_{supine}^{new}$) may be determined as follows:

$$\rho_{prone}^{new} = \rho_{supine}^{new} = 1 - (1-\rho_{prone})*(1-\rho_{supine}) \quad (15)$$

This implies the new scores will be high if at least one of the original CAD classification score is high. Accordingly, this TP booster scheme is shifted towards finding more time positives.

In another example, the new classification scores ($\rho_{prone}^{new}$ and $\rho_{supine}^{new}$) are determined as follows:

$$\rho_{prone}^{new} = \rho_{supine}^{new} = \rho_{prone}*\rho_{supine} \quad (16)$$

This FP suppressor (killer) scheme means that for a pair to receive high score, both scores should be high, which is geared towards reducing more false positives.

Figure 6:
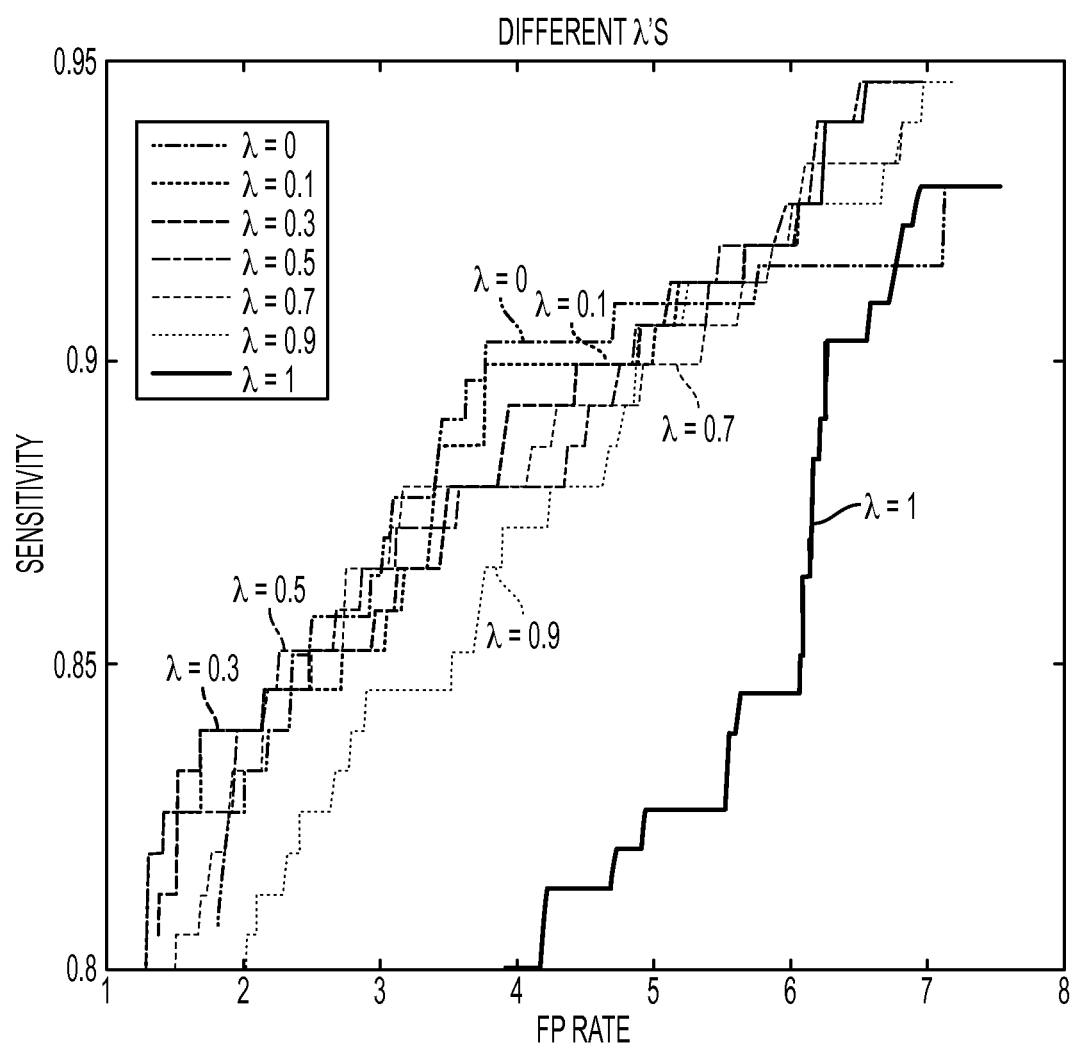
FIG. 6 shows a comparative graph illustrating sensitivity results from varying λ.

In yet another example, a compromise between the above-mentioned two extreme rules is achieved by linearly combining the two original classification scores ($\rho_{prone}$ and $\rho_{supine}$). The new classification scores ($\rho_{prone}^{new}$ and $\rho_{supine}^{new}$) may be determined as follows:

$$\rho_{prone}^{new} = \rho_{supine}^{new} = \lambda*(\rho_{prone}*\rho_{supine}) + (1-\lambda)*(1-(1-\rho_{prone})*(1-\rho_{supine})) \quad (17)$$

where varying $\lambda$ can achieve different trade offs. FIG. 6 shows the results of varying $\lambda$ to obtain various types of compromise between the FP suppressor and the TP booster. As can be observed, when $\lambda$ is closer to 0 (TP booster), the sensitivity is generally higher and the results are more consistent in both the tagged training and testing datasets.

Extensive evaluation was performed using a representative, multi-site clinical database with 195 patient cases in training and 223 cases for testing, containing 106, 118 polyps respectively. The superior performance results on polyp prone-supine view matching was demonstrated by comparing them with existing work mostly based on colon centerline/surface registration. Previous polyp matching techniques are tested and reported on datasets which are at least one order-of-magnitude smaller than the present framework. This is partially because the pair of completely distended prone-supine colon scans (from rectum to cecum) is a prerequisite, and preparing topologically correctly segmented colon cases often requires manual editing or interactions, and can be labor-intensive, given a large number of 3D volumes.

Figure 7A:
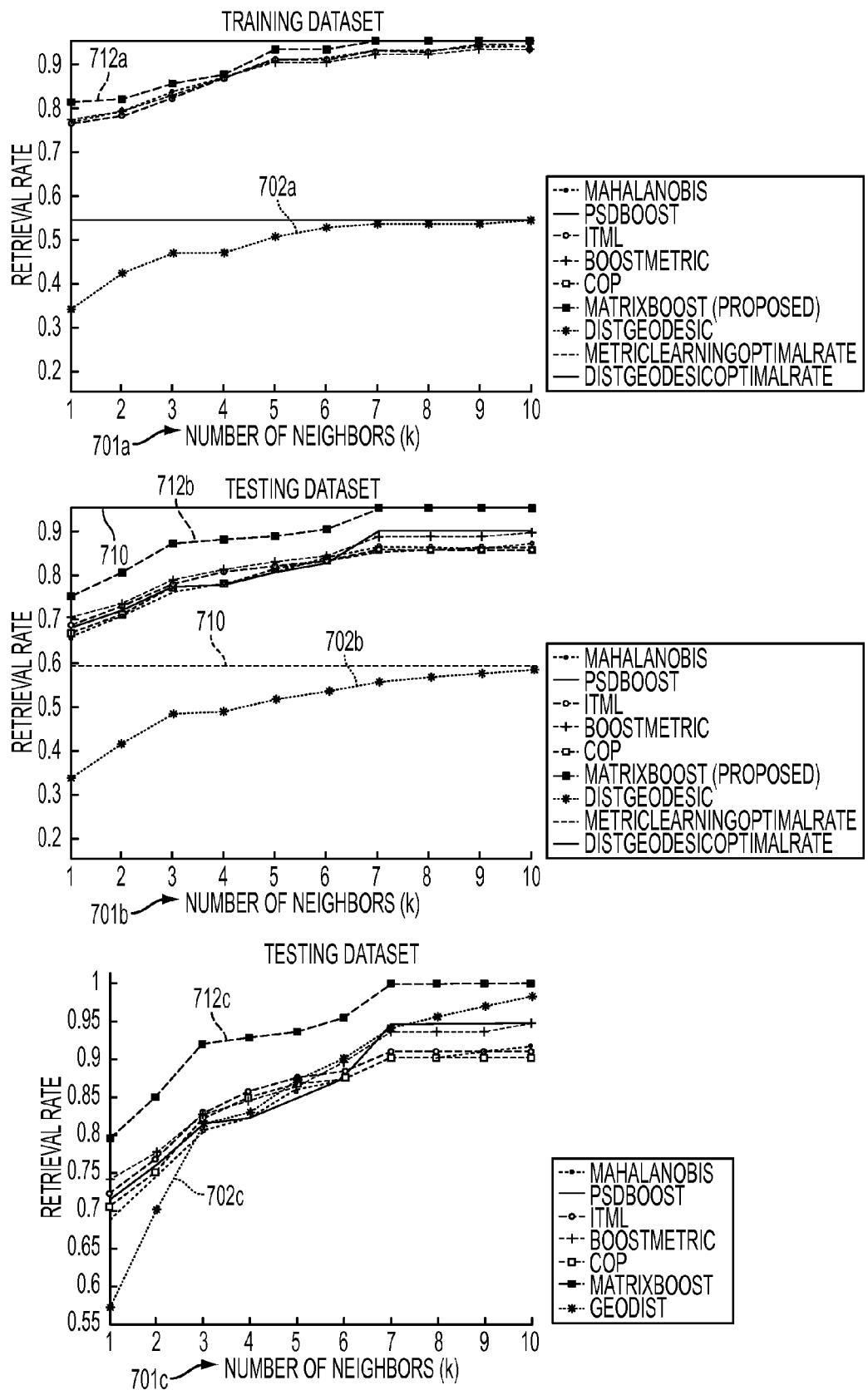
FIG. 7a shows a comparative graph illustrating retrieval rate results according to one aspect of the present disclosure relative to other methods.

FIG. 7a shows three comparative graphs (701a-c) for evaluating the retrieval rates achieved by different methods. Graph 701a shows the retrieval rates based on the training dataset, while graphs 701b-c show the retrieval rates based on the testing dataset respectively. Graph 701c was derived from graph 701b, and shows the retrieval rates normalized with the upper bound retrieval rates (710). By assuming that all polyps are retrievable, pure retrieval accuracies can be compared.

The retrieval rate is defined as the number of polyps retrieved divided by the total number of query polyps. As shown, the retrieval rates generally increased with the increase of the number of neighbors (k). The metric-based learning methods via fusing local polyp appearance features (e.g., Mahalanobis, MatrixBoost, etc.) performed better than centerline Geodesic distance-based retrieval (702a-c). Not all polyps were retrievable given that a small portion of polyps only appeared in a single view, based on ground truth provided by a radiologist. As shown by graphs 701a-b, for the centerline Geodesic distance-based retrieval, more than about 40% polyps were non-retrievable in both training and testing datasets, with the best achievable retrieval rate around 59%. This was in part due to collapsed colon segmentations.

It can also be observed from the graphs (701a-c) that the present MatrixBoost approach (712a-c) dominated the retrieval rates at the full range of k, with a larger margin in the testing dataset. For example, when k=2, the testing retrieval rate of the MatrixBoost method was 80.51%, while the best result of all the other techniques was only 73.73%. High polyp match/retrieval rates with smaller numbers of k can greatly facilitate the workflow for radiologists to match the polyp findings in prone-supine CTC views, Moreover, the present MatrixBoost method permits faster convergence to the upper bounds of polyp retrieval rate at k=7 in both the training and testing datasets.

Figure 7B:
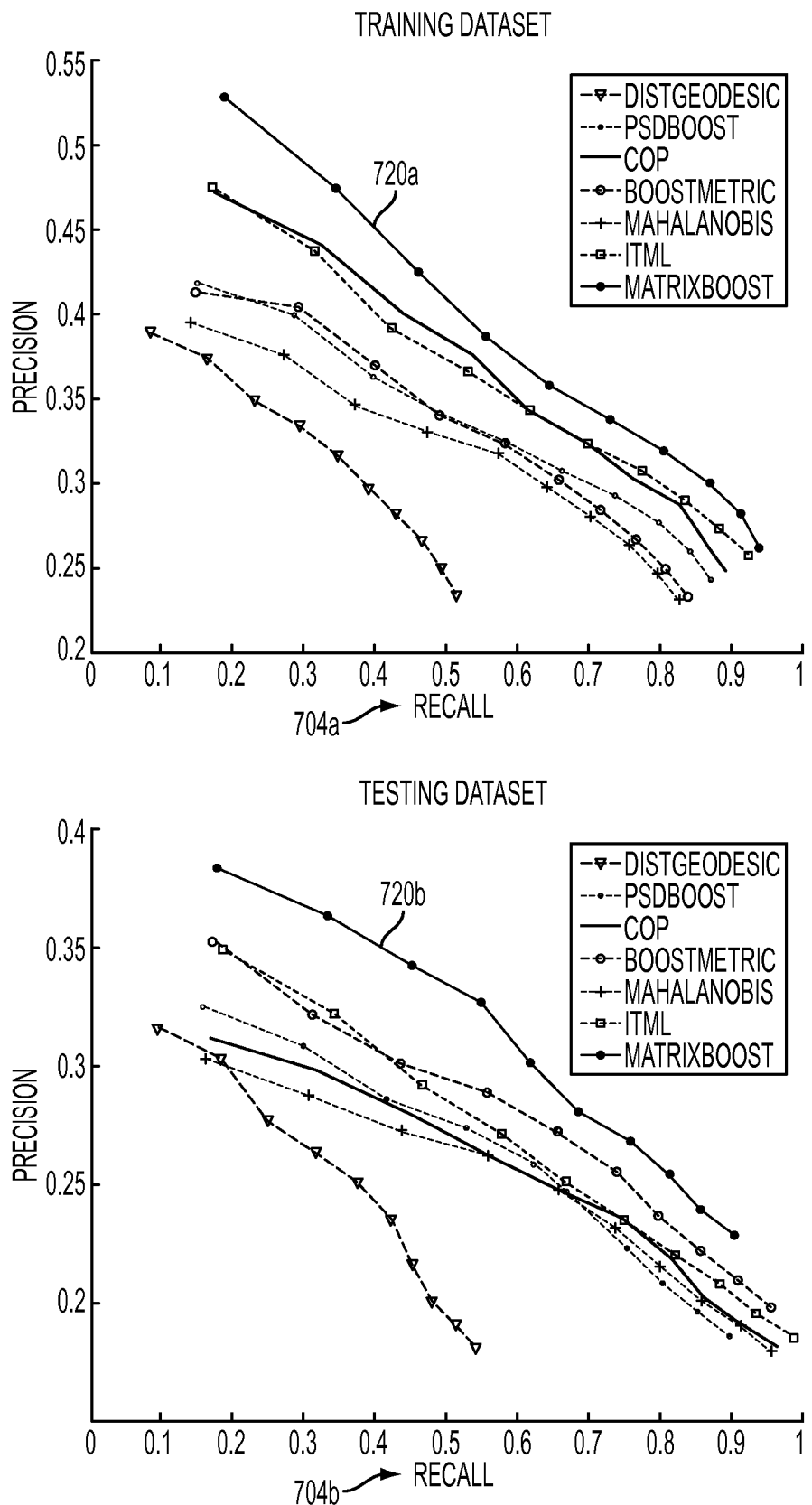
FIG. 7b shows comparative graphs illustrating polyp retrieval Precision-Recall curves according to one aspect of the present disclosure relative to other methods.

FIG. 7b shows two comparative graphs (704a-b) for comparing polyp retrieval Precision-Recall curves using the training and testing datasets respectively. The polyp retrieval Precision-Recall curves show the balance of retrieval accuracy (i.e., the percentage of false pairs retrieved) versus recall. As shown, the present MatrixBoost method (720a-b) significantly outperformed the other metric-based learning and geometric methods.

To evaluate polyp classification, analysis of sensitivity versus FP rate per patient (FROC) was performed. FIG. 8 shows two comparative graphs (802a-b) that compare different matching inductive polyp detection rule-based heuristics (i.e, MatchedThen, FP suppressor, TP booster, compromise between them with $\lambda$=0:5) with a CAD baseline, using the training and testing datasets respectively. As shown, the Matched-Then heuristic (804a-b) performed consistently better than the others, followed by the TP booster heuristic (806a-b). The FP suppressor heuristic required both matched true polyp instances having high classification confidence in both views to be detected, which can be too restrictive (though we can match them robustly). The value of $\lambda$ was varied to control the compromise between FP suppressor heuristic and TP booster heuristic. Empirically, $\lambda$=0 (i.e., TP booster) performed better than FP suppressor heuristic and their compromises on both training and testing datasets.

The Matched-Then rule was used as the default for matching inductive detection. The results based on the testing dataset show that the present framework can increase the sensitivity of CAD baseline by approximately 2 percent (from 0.8903 to 0.9097) when the FP rate is 4. In addition, the present framework can reduce the FP rate per patient by 1.61 (from 5.19 to 3.58) when sensitivity is 0.9097, and reduce FP rate per patient by 1.51 (from 4.778 to 3.268) when sensitivity is 0.8926, which are statistically significant. The CAD baseline compares comfortably or better with other state-of-the-art CAD systems.

FIG. 9 shows two comparative graphs (902a-b) for evaluating the FROC performance of the present MatrixBoost framework with other metric learning techniques, including a convex optimization metric learning method (COP), information theoretic metric learning (ITML) and a BoostMetric method, using CAD baseline as a reference. In general, metric learning methods demonstrated promising results of making polyp matching as a classification module that was helpful for achieving better overall detection. MatrixBoost, ITML and BoostMetric performed similarly in training, but Matrix-Boost was slightly better than others in testing.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

Further, although method or process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

The invention claimed is:

1. A method of matching images using a computer system, comprising:
   receiving, by a processor, first and second digitized images;
   receiving, by the processor, at least one CAD finding corresponding to a detected region of interest in the first image; and
   automatically determining, by the processor, at least one candidate location in the second image that matches the CAD finding in the first image based on local appearance features extracted for the CAD finding and the candidate location, wherein the automatically determining the candidate location comprises learning a distance metric and using the learned distance metric to compute, based on the local appearance features, a distance between the CAD finding in the first image and the candidate location in the second image.

2. The method of claim 1 wherein the first and second images are representative of first and second views of one or more candidate abnormalities of a patient.

3. The method of claim 2 wherein the first and second views comprise a prone, supine, lateral or decubitus view.

4. The method of claim 2 wherein the one or more candidate abnormalities comprise one or more polyps, lung nodules, liver tumors, breast cancer lesions, or prostate tumors.

5. The method of claim 2 wherein the first and second views are acquired at different times.

6. The method of claim 1 wherein the automatically determining the candidate location comprises automatically determining multiple candidate locations in the second image that match the CAD finding in the first image.

7. The method of claim 6 wherein the automatically determining the multiple candidate locations comprises:
   for each candidate location, computing, based on the local appearance features, a distance from the CAD finding in the first image; and
   ranking the multiple candidate locations according to respective computed distances.

8. The method of claim 7 further comprises presenting the ranked candidate locations in a sorted list.

9. The method of claim 1 wherein the learning the distance metric comprises performing metric boosting to optimally combine multiple weak learners to form a strong learner.

10. The method of claim 1 further comprising performing feature selection to select a subset of relevant local appearance features for learning the distance metric.

11. The method of claim 1 wherein the local appearance features comprise intensity, shape, texture-based, geometrical or contextual features.

12. A method of matching images using a computer system, comprising:
   receiving, by a processor, first and second digitized images;
   receiving, by the processor, at least one CAD finding corresponding to a detected region of interest in the first image; and
   automatically determining, by the processor, at least one candidate location in the second image that matches the CAD finding in the first image based on local appearance features extracted for the CAD finding and the candidate location, wherein the automatically determining the at least one candidate location in the second image comprises:
   computing, based on the local appearance features, a distance between the candidate location in the second image and the CAD finding in the first image using a learned distance metric;
   if the computed distance is less than a predetermined distance threshold, identifying the candidate location as a true candidate.

13. The method of claim 12 wherein if the computed distance is more than a predetermined distance threshold, identifying the candidate location as belonging to a class determined by a first classification score.

14. The method of claim 13 further comprising identifying the candidate location as a false candidate if the first classification score is less than a predetermined score threshold.

15. The method of claim 13 further comprising computing the first classification score by combining second and third classification scores associated with the CAD finding and the candidate location respectively.

16. The method of claim 15 wherein the computing the first classification score comprises computing $1-(1-\rho_{prone})*(1-\rho_{suppine})$, wherein $\rho_{prone}$ denotes the second classification score and $\rho_{supine}$ denotes the third classification score.

17. The method of claim 15 wherein the computing the first classification score comprises multiplying the second and third classification scores.

18. The method of claim 15 wherein the computing the first classification score comprises computing $\lambda*(\rho_{prone}*\rho_{supine})+(1-\lambda)*(1-(1-\rho_{prone})*(1-\rho_{supine})$, wherein $\rho_{prone}$ denotes the second classification score, $\rho_{supine}$ denotes the third classification score and $\lambda$ denotes a trade-off variable.

19. A method of matching images across multiple views using a computer system, comprising:
   receiving, by a processor, digitized training images representative of at least first and second views of one or more regions of interest;
   performing, by the processor, feature selection based on the training images to select a subset of relevant local appearance features to represent instances in the first and second views; and learning, by the processor, a distance metric based on the subset of local appearance features, wherein the distance metric comprises a boosted distance metric.

20. The method of claim 19 wherein the boosted distance metric comprises a Mahalanobis distance metric.

21. The method of claim 19 wherein the learning the distance metric comprises performing metric boosting to optimally combine multiple weak learners to form a strong learner.

22. The method of claim 21 wherein the weak learners are constrained by an equivalence relationship.

23. The method of claim 21 wherein the weak learners are constrained by a proximity relationship.

24. The method of claim 21 wherein the weak learners comprise low rank positive semi-definite (PSD) matrices.

25. The method of claim 21 wherein an AdaBoost method is performed to combine the multiple weak learners.

26. The method of claim 19 wherein the performing the feature selection comprises performing a Minimum Redundancy Maximum Relevance (MRMR) method.

27. The method of claim 19 wherein the local appearance features comprise intensity, shape, texture-based, geometrical or contextual features.

28. A system for matching images, comprising:
 a memory device for storing non-transitory computer readable program code; and
 a processor in communication with the memory device, the processor being operative with the computer readable program code to:
  receive first and second digitized images;
  receive at least one CAD finding corresponding to a detected region of interest in the first image; and
  automatically determine at least one candidate location in the second image that matches the CAD finding in the first image based on local appearance features for the CAD finding and the candidate location, wherein the automatically determining the candidate location comprises learning a distance metric and using the learned distance metric to compute, based on the local appearance features, a distance between the CAD finding in the first image and the candidate location in the second image.

29. A non-transitory computer readable medium embodying a program of instructions executable by machine to perform steps for matching images, the steps comprising:
 receiving first and second digitized images;
 receiving at least one CAD finding corresponding to a detected region of interest in the first image; and
 automatically determining at least one candidate location in the second image that matches the CAD finding in the first image based on local appearance features for the CAD finding and the candidate location, wherein the automatically determining the candidate location comprises learning a distance metric and using the learned distance metric to compute, based on the local appearance features, a distance between the CAD finding in the first image and the candidate location in the second image.

* * * * *